US011842272B2

(12) United States Patent
Ursella et al.

(10) Patent No.: US 11,842,272 B2
(45) Date of Patent: Dec. 12, 2023

(54) COMPUTER-IMPLEMENTED METHOD FOR TRAINING OR USING A SOFTWARE INFRASTRUCTURE BASED ON MACHINE-LEARNING TECHNIQUES

(71) Applicant: MICROTEC S.R.L., Bressanone (IT)

(72) Inventors: Enrico Ursella, Mestre (IT); Davide Boschetto, Vigonza (IT); Federico Giudiceandrea, Bressanone (IT)

(73) Assignee: MICROTEC S.R.L., Bressanone (IT)

( * ) Notice: Subject to any disclaimer, the term of this patent is extended or adjusted under 35 U.S.C. 154(b) by 738 days.

(21) Appl. No.: 17/023,579

(22) Filed: Sep. 17, 2020

(65) Prior Publication Data

US 2021/0089902 A1    Mar. 25, 2021

(30) Foreign Application Priority Data

Sep. 24, 2019    (IT) .......................... 102019000017138

(51) Int. Cl.
| | |
|---|---|
| *G06N 3/08* | (2023.01) |
| *G06T 7/73* | (2017.01) |
| *B27B 1/00* | (2006.01) |
| *G06T 7/00* | (2017.01) |
| *G06V 10/44* | (2022.01) |

(52) U.S. Cl.
CPC ............... *G06N 3/08* (2013.01); *B27B 1/007* (2013.01); *G06T 7/0004* (2013.01); *G06T 7/73* (2017.01); *G06V 10/454* (2022.01); *G06T 2207/10116* (2013.01); *G06T 2207/20081* (2013.01); *G06T 2207/30161* (2013.01)

(58) Field of Classification Search
CPC .......... G06N 3/08; G06N 3/045; B27B 1/007; G06T 7/0004; G06T 7/73; G06T 2207/10116; G06T 2207/20081; G06T 2207/30161; G06V 10/454; G06V 10/774; G06V 10/82; G01N 23/046; G01N 33/46
See application file for complete search history.

(56) References Cited

U.S. PATENT DOCUMENTS

| | | | |
|---|---|---|---|
| 10,571,454 B2* | 2/2020 | Narasimhan | G06T 7/0004 |
| 2012/0022829 A1 | 1/2012 | Giudiceandrea et al. | |
| 2019/0227049 A1 | 7/2019 | Narasimhan et al. | |
| 2020/0191765 A1* | 6/2020 | Narasimhan | G06T 7/0004 |
| 2021/0019873 A1* | 1/2021 | Ursella | G06N 20/00 |
| 2021/0383565 A1* | 12/2021 | Le | G16H 30/40 |

FOREIGN PATENT DOCUMENTS

| | | |
|---|---|---|
| EP | 2410328 B1 | 12/2014 |
| WO | 2018169712 A1 | 9/2018 |

OTHER PUBLICATIONS

Boukadida, H., et al., "Pith Extract: A Robust Algorithm for Pith Detection in Computer Tomography Images of Wood Application to 125 Logs From 17 Tree Species", Computers and Electronics in Agriculture, Elsevier, Amsterdam, The Netherlands, vol. 85, Mar. 31, 2012, pp. 90-98.

Zhu, D., et al., "A Computer Vision System for Locating and Identifying Internal Log Defects Using CT Imagery", Proceedings, 4th International Conference on Scanning Technology in the Wood Industry, Oct. 28, 1991, pp. 1-13.

* cited by examiner

*Primary Examiner* — Bobbak Safaipour

(74) *Attorney, Agent, or Firm* — Pearne & Gordon LLP; J. Gregory Chrisman

(57) ABSTRACT

A computer-implemented method for training a software infrastructure based on machine-learning techniques to analyse data obtained from a instrumental examination of objects of a predetermined type, where each of the objects has been obtained by splitting a product into smaller pieces, wherein the software infrastructure receives, for each object in a training set, training input data comprising the data obtained from the instrumental examination and training output data comprising information on the characteristics of interest of the training object, wherein the information on the characteristics of interest is, at least in part, information that has been obtained from the results of a tomographic examination of the product from which the training object was obtained, and wherein the software infrastructure processes, through its own training unit, the training input data and the training output data for each training object in order to set internal processing parameters for the software infrastructure which correlate the training input data to the training output data.

21 Claims, No Drawings

COMPUTER-IMPLEMENTED METHOD FOR TRAINING OR USING A SOFTWARE INFRASTRUCTURE BASED ON MACHINE-LEARNING TECHNIQUES

The present invention relates firstly to a computer-implemented method for detecting characteristics of interest of an object of a predetermined type using a software infrastructure based on machine-learning techniques and which uses, as input data, data obtained from carrying out an instrumental examination of the selected object, and particularly to the method used for training the software infrastructure, where the relevant object is obtained from splitting a larger parent product.

The invention in question was initially developed in reference to the timber processing sector, with the aim of increasing the efficiency of the computer systems that can be used to test the quality of boards obtained from sawmilling. Reference will therefore be made to that sector below.

Nevertheless, the present invention should also be considered to be aimed at any other sector in which similar needs are felt. For example, it may be used in relation to the following products:
  meat;
  cured meat, sausages or cheese;
  bread;
  stone materials (e.g. marble).

As mentioned above, the present invention aims to use, as starting data, only information that can be obtained from carrying out an instrumental examination of the finished object (boards in the case of timber). In particular, the present invention aims to use, as starting data, information obtained from carrying out an instrumental examination of the finished object, which can be shown as two-dimensional images, such as surface images or x-ray images. Furthermore, the present invention aims to obtain information, by examining the results of the instrumental examination, on characteristics of the object which cannot currently be obtained with sufficient precision by currently known algorithms. Indeed, the information which the present invention aims to obtain could easily be obtained at present by performing a tomographic examination of each object; however, tomographic examinations are not among the instrumental examinations which the present invention wishes to use the results of.

As is known, tomography is a technology that allows the internal structure of a product to be analysed by processing x-ray images taken from different angles.

Currently, tomography is mainly applied to the field of medicine, in airport baggage checks, in scientific testing and in sample-testing of quality in manufacturing.

One application that has been gaining ground in recent years is the use of this testing to optimise subsequent stages of processing. As mentioned at the beginning of this description, applications in this field include use in timber processing facility (sawmills) and, in particular, the use of tomography in optimising sawmilling for the production of boards.

Developing automatic inspection and calculation systems for an optimal sawing pattern requires software that is capable of accurately, quickly and automatically analysing the tomographic images produced in order to correctly predict the quality and characteristics of the by-products (boards) that can be obtained once the starting material (log) has been processed. The quality of the by-products will depend, for instance, on their internal structure (e.g. the presence or absence of defects such as knots in wood intended for structural purposes) or on their appearance (in wood intended for "aesthetic" purposes).

In the context of the present invention, the terms "tomographic images" and "data obtained from a tomographic examination" should be considered synonyms and therefore interchangeable, as tomographic images are merely the graphic reproduction of that data.

For several years, computed tomography has been used on logs for the purpose of optimising sawmill production. The CT Log scanner is a tomographic scanner produced and marketed by this same applicant, which is able to carry out log tomography at speeds of up to 180 m/min, calculate a model of the internal features of each log and optimising the entire subsequent sawing process based on the raw material characteristics and the sawmill's production requirements (Giudiceandrea, F., Ursella, E., & Vicario, E.—2011, September—. A high speed CT scanner for the sawmill industry. In Proceedings of the 17th international non destructive testing and evaluation of wood symposium—pp. 14-16. Sopron, Hungary: University of West Hungary).

Several publications have demonstrated the economic benefit of optimising the sawmilling process using tomographic imaging of logs (Rais, A., Ursella, E., Vicario, E., & Giudiceandrea, F. (2017). The use of the first industrial X-ray CT scanner increases the lumber recovery value: case study on visually strength-graded Douglas-fir timber. Annals of forest science, 74 (2), 28; Berglund, A., Broman, O., Grönlund, A., & Fredriksson, M. (2013). Improved log rotation using information from a computed tomography scanner. Computers and electronics in agriculture, 90, 152-158; Stängle, S. M., Brüchert, F., Heikkila, A., Usenius, T., Usenius, A., & Sauter, U. H. (2015). Potentially increased sawmill yield from hardwoods using X-ray computed tomography for knot detection. Annals of forest science, 72 (1), 57-65).

Several studies have addressed the issue of automatically detecting the internal characteristics of logs, particularly knots, based on tomographic images (Andreu, Jean-Philippe, and Alfred Rinnhofer. "Modeling of internal defects in logs for value optimization based on industrial CT scanning." Fifth International Conference on Image Processing and Scanning of Wood. Bad Waltersdorf Austria, 2003; Breinig, L., Brüchert, F., Baumgartner, R., & Sauter, U. H. (2012). Measurement of knot width in CT images of Norway spruce (*Picea abies* [L.] Karst.)—evaluating the accuracy of an image analysis method. Computers and electronics in agriculture, 85, 149-156; Fredriksson, M., Cool, J., Duchesne, I., & Belley, D. (2017). Knot detection in computed tomography images of partially dried jack pine (*Pinus banksiana*) and white spruce (*Picea glauca*) logs from a Nelder type plantation. Canadian Journal of Forest Research, 47 (7), 910-915; Cool, J., Fredriksson, M., & Avramidis, S. (2017). Knot detection in coarse resolution CT images of logs. In 23rd International Wood Machining Seminar, Warsaw, Poland, 28-31 May 2017; Longuetaud, F., Mothe, F., Kerautret, B., Krähenbühl, A., Hory, L., Leban, J. M., & Debled-Rennesson, I. (2012). Automatic knot detection and measurements from X-ray CT images of wood: a review and validation of an improved algorithm on softwood samples. Computers and Electronics in Agriculture, 85, 77-89.).

All of these studies, among others, have demonstrated how, by using software instruments, tomographic images can be used to determine many of the characteristics of the material itself (e.g. finding whether materials are made of wood rather than air or resin pockets, identifying the direction of wood fibres, understanding whether sapwood or hardwood is present, finding whether knots are living or dead, etc.) or of the log (meaning the three-dimensional—e.g. pith position, knot position, bend, etc.). Therefore, by developing new analytical techniques, it is within reason that ever more information will be obtainable from tomographic imaging of each log.

However, given the high costs of the technology, tomographic scanners are not present in all facilities. Nevertheless, where these scanners are not present, tomographic scans can still be performed beforehand in another establishment and the data can be provided to the facility together with the log.

In most board sawmilling lines, on the other hand, control stations are located downstream from the sawing mechanism, and house a device which automatically examines each board so as to detect the selected board characteristics which are to be used later to classify the board for commercial purposes. Advantageously, these devices are able to perform several different types of instrumental examinations.

One example of a control station capable of performing multiple board instrumental examinations is that marketed by this applicant under the Goldeneye® brand.

Although these control stations are already remarkably high-performing, the constant market demand for more and newer information concerning board quality means that they are not yet able to identify all potentially desirable characteristics.

For instance, certain classification methods adopted in North America require each knot on each board to be evaluated based on its performance within the board rather than on its appearance only. This information cannot be easily deduced from a two-dimensional examination of the board (but from a tomographic examination only). However, since knots are always arranged radially from the trunk's pith, just knowing the pith's position relative to the board in question would enable virtually every surface knot to be projected internally, which would in turn allow for a more precise board classification.

Knowing the pith's position in the parent log relative to each board obtained from the log is therefore potentially important for assessing its value.

Another case in which it is important to know the pith's position is when boards are to be used to make window profiles. Indeed, the presence of the pith on the profile surface is unacceptable to the industry, as the pith is softer than the surrounding wood and is therefore more prone to damage. Knowing the position of the pith before processing the boards can therefore allow waste to be avoided.

However, automatically (using processing software) determining the position of the pith based on surface images, or based on the results of other two-dimensional instrumental examinations currently performed on boards, brings difficulties; although a large volume of information can be obtained from the results of instrumental examinations (the relative position of knots, grain widths), it is extremely difficult to codify an algorithm that is able to correctly deal with all cases that may arise.

Other information easily identifiable in a tomography, but which is more difficult to identify from non-tomographic board instrumental examinations, can include the direction of the grain or fibre, the presence of bark inclusions and the presence of bluing.

As is known, one technique that is increasingly being developed to independently examine the content of images is machine learning.

Machine learning refers to a series of techniques used to train a computer to independently determine information based on an initial data set.

This training is usually based on a mathematical algorithm implemented on a dedicated software infrastructure into which numerous examples of images, each labelled according to selected criteria, are fed. A portion of these examples (the training set) is algorithm tested in order to independently set a series of internal algorithm parameters, with algorithms also used to optimise the result obtained (for error minimisation).

Once the system has optimised its own parameters, it is tested on another group of known examples (the test set) to assess the system's ability to operate in new situations; if a favourable response is obtained—i.e. if the results are as expected—then the system can finally be used on an industrial level.

The above description of methods of training a software infrastructure based on machine-learning techniques, must also be held to apply to the training method which is the object of this invention.

Until a few years ago, the machine-learning techniques applied to image recognition were purely based on preliminary image processing, during which pre-set characteristics were calculated from each part of the image (e.g. gradients, statistical distribution of pixel groups, SIFT, etc.); the results of this preliminary processing were then passed to a classifier (e.g. Bayes, SVN, random forest) that had previously been trained using examples (each consisting of the desired input and corresponding output data) to calculate parameters which were capable of correctly classifying whole or partial images.

In recent years, there has been a rise in deep-learning techniques, which use deep neuronal networks (i.e. with more layers than the 2 or 3 layers used previously) and, in particular, convolutional neural networks, which have proved to be particularly suitable for analysing images. Convolutional neural networks (CNNs) are mathematical algorithms that use one or more digital images as the input and are typically able to give as an output either a classification of the entire image (e.g. image of a car, cat, person's face, etc.), a classification of each image pixel (main object pixel—person, car, animal; or background pixel—sky, floor, etc.) or a classification of areas of the image that share common characteristics (e.g. by segmenting the image into a building area, a sky area, a pavement area, etc.; the process of splitting an image into coherent pixel areas is called semantic segmentation).

Several types of CNNs exist both in literature and in software. In many applications, CNNs are made up of several consecutive processing layers (or levels). Within each layer, the following can be applied to the input data: convolutions with one or more kernels (with learned values—as decided by the CNN in the training phase); linear or non-linear functions (e.g. $\max(x,0)$ $\min(x,0)$, etc., where x is the value under consideration); or subsampling functions. In all machine-learning applications relevant for the present invention, several levels are consecutively activated for each processing operation, with each level—except the first level—using as its input the output from the level before it. The data in each level are then processed according to a programmer-selected combination of several mathematical functions; this can be linear functions, non-linear functions or a combination of both.

In general, to create a specialised neural network for a given functionality, a programmer is required to define the "hyperparameters" only, such as the number of layers, the number of convolutions for each layer, or the size and span of the convolution kernels. It is necessary to feed into the CNN a sufficient number of examples in which both the input and the desired output are known.

Several software infrastructures are currently available which are capable of running a CNN and optimising the calculation of internal network parameters (those used by each function) during the training step in such a way as to best resolve the task assigned.

In recent years, the scientific community and many private investors have made huge investments in this field, to such an extent that there are currently several tools available which enable network software infrastructure to be built, to be trained (i.e. made to "learn" the optimal network parameters) and to perform inference (i.e. to use the network to analyse unknown data once the network has been trained).

Notable examples include TensorFlow and Caffe.

The main difficulty that arises in the actual use of machine-learning systems in general, and deep neural networks (such as CNN) in particular, concerns the need for an extremely large number of carefully selected examples to be available so that a system can learn its parameters correctly. The more complex the problem being faced, the higher the number of examples required.

Whereas only a few hundred examples may be sufficient when applying traditional algorithms to fairly straightforward problems, the latest CNNs have proved capable of resolving more difficult problems, but only if they have thousands, tens of thousands or sometimes even millions of examples available to use during the training step.

Until now, to enable the development of networks capable of performing accurate image analysis, the main solution adopted has been to use large numbers of people to look at and classify images; in this respect, then, it has now become somewhat possible to teach computers the ability of the human brain when it comes to analysing images.

It is worth noting that once a software infrastructure has been trained once for a given piece of equipment, this can be replicated in any other structurally identical equipment.

The innovative conception underlying the present invention was to develop an innovative based on machine-learning techniques method of training a software infrastructure, which is in turn associated to a corresponding method of creating a large—even potentially infinite—database of examples to be used for training.

As an example, creating a large database of board images in which the position of the trunk's pith can be determined would enable the creation of a database for teaching an independent machine-learning system how to determine the pith's position.

However, creating this database would be very complicated because, on the one hand, it would require images of a great number of boards to be acquired (to be used as input data) and, on the other hand, it would require each of these boards to be examined, perhaps even by physically slicing them to identify the position of the trunk's pith.

Therefore, in the context described herein, the technical task of the present invention was to devise a computer-implemented method for training a software infrastructure based on machine-learning techniques to analyse data obtained from a instrumental examination of objects of a predetermined type of objects in order to determine information on characteristics of interest of those objects.

A further technical task of the present invention was to devise a method which would enable a large (numerous) database of known examples to be created (were the results of the instrumental examinations and the information on the characteristics of interest are known for each example) for use in training a software infrastructure based on machine-learning techniques.

At least some of the technical tasks stated above are achieved by the description contained in the accompanying claims, with the applicant nevertheless reserving the right herein to have other innovative aspects described in the present description protected separately, including by depositing subsequent divisional patent applications.

Further features and the advantages of the present invention will become more apparent after a careful reading of the detailed description of several preferred, non-limiting embodiments of the present invention.

As mentioned above, the present invention has been developed in the context of a computer-implemented method enabling the detection of characteristics of interest of objects of a predetermined type. The preferred, but non-limitative, application of the present invention relates to the case where the objects are boards obtained from the sawmilling of logs.

The computer-implemented method involves the use of a software infrastructure based on machine-learning techniques, preferably a software infrastructure that includes a neural network, a deep neural network, a convolutional neural network or a combination of two or more of the above.

According to the present invention, the software infrastructure (in particular its processing unit) is programmed in such a way that the input data shall be the data obtained from the instrumental examinations of the object, which shall include a multi-faceted instrumental examination so as to detect various aspects of the object. As an example, in the preferred embodiments, the instrumental examination comprises one or more of the following:

acquiring images of one or more surfaces of the object, on one or more wavelength bands, within the visible light range and/or in other ranges such as infrared or ultraviolet;

projecting beams of electromagnetic radiation onto the object's surface and acquiring images of the surface itself to detect the propagation of light radiation in the object's material (e.g. localised light on the board surface to indicate the presence of scattering);

performing x-rays of the object;

analysing own vibration frequencies following a stress event.

In general, however, the data obtained from the instrumental examination are in electronic format and may advantageously correspond to images of the object's surface within the visible light range on one or more wavelength bands, to images of the surface outside the visible light range on one or more wavelength bands, to images of the surface illuminated to highlight presence of propagation (such as wood scattering), to images obtained by performing x-rays of the object, to combinations of one or more of the above, or to measurements of the object's vibration frequency spectrum (obtained, for instance, using a microphone or laser interferometer).

In a preferred embodiment, however, the input data consist of one or more groups of electronic data, wherein each group is the electronic depiction of a two-dimensional image (i.e. a two-dimensional array of pixels).

In this case, the data obtained from the instrumental examination thus advantageously consist of a two-dimensional electronic map depicting the object or a part thereof, with the electronic map comprising a plurality of cells (the pixels, in the case of an image) with at least one value assigned to each.

As already mentioned, like all software infrastructures based on machine-learning techniques, the software infrastructure described in the present invention requires—in addition to developing the infrastructure itself according to common methods for developing this type of software (which are known per se and are not therefore described further here)—preventive training of the infrastructure during which the infrastructure gradually optimises its internal calculation parameters by serially analysing a large number of examples for which training input data are available, which must be qualitatively analogous to those that the infrastructure will use when fully operational, and training output data which must match the output data that are to be provided by the network when fully operational based on the training input data fed in.

It is with this purpose in mind that the main innovative aspect of the present invention has been developed, with regard to the computer-implemented method for training a software infrastructure based on machine-learning techniques intended to analyse data obtained from a instrumental examination of objects of a predetermined type of objects in order to determine information on characteristics of interest of those objects.

To implement the method for training a software infrastructure, according to the present invention each object which is to be used to generate the training input data must be obtained by splitting a larger product for which tomographic examination data are available into smaller pieces (however, tomographic examination need not be performed in the context of the method described in the present invention, even where it may be possible to do so).

The training method first requires a training set to be selected which comprises a plurality of training objects of the same pre-determined type (for instance, boards), which must have been obtained by splitting up a larger product (such as a log) for which tomographic examination data are available. The objects having the same pre-determined type may also mean that they have the same intrinsic characteristics, which the software infrastructure must take into consideration when in operation; for instance, where applied to wooden boards that are of the same pre-determined type, this may also mean that they are made of the same type of wood (or even of the same type of wood from the same forest) and/or that they have the same dimensions.

According to a first embodiment of this method, once the training set has been selected, the training input data and the corresponding training output data are fed into the software infrastructure, more particularly into a training unit, for each object.

As mentioned above, the training input data for each training object comprise the data obtained from the instrumental examination on that training object.

On the other hand, the training output data for each training object comprise information relating to the characteristics of interest of the training object. According to the present invention, the information on the characteristics of interest is obtained from the results of the tomographic examination of the product from which the training object was obtained. While in some cases the information can be obtained automatically by using software for analysing the results of the tomographic examination, in other cases the involvement of an operator or another device may also be required to interpret, confirm and/or integrate the information that can be obtained from the tomographic examination.

For instance, where wood-bleaching is present, an operator may be required to manually check the areas previously identified from the tomographic examination before the training output data can be defined.

Subsequently, by processing the training input data and the training output data for each object in the training set, the software infrastructure—using its own specifically programmed training unit—sets its own internal processing parameters in such a way for there to be a correlation between the training input data and the training output data (naturally, this correlation will always be checked unless a certain margin of error is considered—or defined as—acceptable).

The software infrastructure can be programmed to provide different results (output data) based on the different embodiments.

In a first application, for instance, it can be programmed to produce as output data a classification of each object to a specific class. This class will preferably be chosen from a group of possible pre-set classes. If the characteristics of interest refer to the position of wood characteristics or defects on the board, then each class will advantageously correspond to such position being within a space volume located inside or outside of the board. For instance, several cases may arise with reference to the position of the trunk's pith relative to a board: pith outside the board; pith in the centre of the board; pith near a surface of the board; pith in an intermediate position between the centre and the outside surfaces.

In some embodiments, the classification may also be expressed as a probability that the object belongs to each specific class.

According to a second application, the software infrastructure may provide information on a specific aspect of the object as output data. For boards, for instance, it may indicate the position of the trunk's pith relative to the board. Since the pith mainly extends longitudinally along the board, its position relative to the board can be defined by referring to its position in a cross-section of the board. Furthermore, the position in the cross-section can be identified both quantitatively (e.g. by measuring the distance from the surfaces) and qualitatively (e.g. by dividing the cross section into a grid—3×3 cells is considered sufficient for each board—and identifying the cell in which the pith is located, or by allocating a probability of the pith's presence to each cell). Clearly, it is also possible that the pith will not be located inside the board, in which case its position relative to the board can still be of interest for identifying the direction in which knots develop.

Where the characteristics of interest may vary within the object (for instance, where the pith's position relative to a board may change as the board extends longitudinally), the software infrastructure can also be programmed to provide multiple output data, such as by analysing portions of the objects as it goes along (e.g. successive longitudinal sections of a board, including partially overlapping if necessary).

In other embodiments, the software infrastructure can be programmed to also provide output data obtained from more complex processing (e.g. knot volume, calculated by taking into account the pith's position and the surface area covered by the knots on each surface; or calculations of the board's elastic modulus).

For applications in the wooden board sector, the characteristics of interest may advantageously correspond to the presence or not on the board of wood features or defects and/or to the position of these characteristics or defects relative to the board.

As already mentioned, when training the software infrastructure according to the present invention, the training output data are at least partly obtained from the results of the tomographic examination of the product from which the objects were obtained; in other words, whether the results were obtained exclusively from the results of the tomographic examination (perhaps supplemented with prior information on the nature of the objects), or whether other entities (people or equipment) were involved in preparing these results. In the event of a more complete embodiment, the computer-implemented method for training a software infrastructure also comprises a sequence for preparing training output data, which includes a tomography step, a splitting step, a correlation step and a processing step.

In the tomography step, a tomographic examination of a product is performed using an electronic tomograph, from which the results of the tomographic examination are obtained.

In the splitting step, the product is split into a plurality of different trained objects; this step is advantageously performed using a mechanical device, such as with a saw in the case of board production.

In the correlation step, which is computerised, each training object obtained from splitting the initial product as above is correlated to its position within the product the training object has been obtained from and/or to at least part of said results of the tomographic examination of the product the training object has been obtained from. For applications in the board production sector, this can be achieved by means of the known techniques of continuous tracking or subsequent board recognition (either identifying elements applied to each table or board-specific characteristics—i.e. fingerprints—may be used for this purpose).

Finally, the processing step is also computerised. Based on the results of the correlation step, the results of the tomographic examination are processed to determine information on the characteristics of interest of each training object. By way of example, once the position of the board in the log the board has been obtained from is known, the position of the pith in the log can be first determined in the processing phase; by combining these positions, the pith's position relative to the board can then become known.

According to a further innovative aspect of the present invention, the training method can include the initial training of the software infrastructure, at the end of which the software infrastructure can be used in industry with satisfactory results, and this will then be followed by subsequent improvement/refinement training aimed at further enhancing the performance of the software infrastructure. According to the preferred embodiment, the improvement/refinement training is advantageously performed while the software infrastructure is in ordinary use; once available, the results (the new parameters) are used directly during the subsequent use of the processing unit.

In particular, the improvement/refinement training can be performed highly advantageously in the context of facilities for the production of objects of the pre-determined type, in which the objects are obtained by splitting an initial product into several smaller pieces and in which the quality of each object is verified using a instrumental examination, provided that data from a tomographic examination are available for each initial product.

Advantageously, therefore, one or more management and control computers at the object's processing facility generate the training output data by processing the tomographic data without interrupting the processing facility's operation, and these output data are then used by the training unit together with the training input data generated for the same object to set internal processing parameters for the software infrastructure, which correlate the training input data to the training output data. All of the above should occur during the ordinary operation of the facility.

The above is an example of how a more general embodiment of the computer-implemented training method described in the present invention is applied, which includes an initialisation step in which the training set is created which comprises a plurality of objects of a predetermined type and a plurality of expansion steps in which one or more objects of the predetermined type are added to the training set, and wherein the training unit processes the training input data and the training output data for each object in the training set in order to set internal processing parameters for the software infrastructure which will correlate the training input data to the training output data both after the initialisation step and after each expansion step. In other words, the training of the software infrastructure is repeated after each expansion of the training set; on each occasion, it uses the previously determined parameters as its initial parameters and sets the new parameters based on the objects added only.

As in the example above, the objects added to the training set in each expansion step are advantageously objects to which the software infrastructure—through its own processing unit—has previously applied machine-learning techniques to analyse the data obtained from the instrumental examination on those same objects for the purpose of determining information on the characteristics of interest of those objects (using the parameters set until that point). This applies, for instance, to facilities in which all boards are verified by apparatuses such as the aforementioned Goldeneye®, which is produced by the applicant.

Therefore, in a particularly preferred embodiment, the computer-implemented training method described in the present invention is implemented by one or more management and control computers in a product processing facility. This facility will comprise one cutting station in which each product is split into a plurality of objects, and a control station in which one or more instrumental examinations are performed on the objects obtained by splitting the product, thus obtaining the input data for the objects.

Advantageously, the software infrastructure is linked to the control station and also comprises a processing unit. This processing unit uses the internal processing parameters set by the training unit to determine information on the characteristics of interest of the object by correlating the input data, obtained in the control station for each object, to the output data.

In more complete embodiments, the method is implemented in a facility which, located upstream from the cutting station, also comprises a tomography station in which a three-dimensional tomographic examination is performed on each product before being split into several objects. In this case, then, the training output data for each object are obtained from one or more management and control computers by processing the results given by the tomography station.

Advantageously, however, once the facility is operational and the software infrastructure has been sufficiently trained, he training input data and the training output data are generated for each object without interrupting the operation of the processing facility, and these data are used by the training unit of the software infrastructure during the ordinary use of the facility in order to perform a further set of the internal processing parameters of the software infrastructure (which can be considered the final setting).

Naturally, the scope of the present invention also includes a computer-implemented method for detecting characteristics of interest of an object of a predetermined type, wherein the computer-implemented method includes the use of a software infrastructure based on machine-learning techniques, wherein the software infrastructure uses as the input data the electronic data obtained from a instrumental examination on the relevant object to provide, as the output data, the characteristics of interest of the object, and wherein the software infrastructure used has been trained according to the above description.

Finally, the scope of the present invention also includes a facility for manufacturing objects of a predetermined type by splitting up a larger product and, in particular, for making boards from logs, with this facility comprising at least the following:
- one or more management and control computers (connected to all parts of the facility);
- one cutting station in which each product is split into a plurality of objects; and
- one control station in which one or more instrumental examinations are performed on the objects obtained from splitting the initial product.

Advantageously, upstream from the cutting station, the facility also includes a tomography station wherein the three-dimensional tomographic examination of each product is performed, even if it may alternatively be arranged that the results of a previously performed three-dimensional tomographic examination will be used.

The one or more control computers implement a method for detecting the characteristics of interest of each object, which involves using a software infrastructure based on machine-learning techniques that uses as the input data the information obtained from the instrumental examination on each object. The software infrastructure is also trained using a computer-implemented training method, as described above, and provides, as the output data, the characteristics of interest of the object.

Finally, the input data—i.e. the data generated by the control station for at least some of the objects processed in the facility—are advantageously used by the one or more management and control computers to perform—through the training unit—continuous training of the software infrastructure during the ordinary use of the facility (e.g. according to the methods indicated above).

The present invention offers significant advantages.

Indeed, the present invention has made it possible to develop a software infrastructure based on machine-learning techniques that is able to use the results of the two-dimensional instrumental examinations performed on objects to determine characteristics thereof that cannot be determined using currently known techniques.

Moreover, the present invention allows the software infrastructure to be comprehensively trained using a large number of cases in a single installation, which can then be duplicated for any other similar installation.

Many modifications and variations can be made to the invention as designed herein without departing from the scope of the present invention.

All details can be replaced by other technically equivalent details and any materials, shapes and dimensions of the various components may be used according to requirements.

The invention claimed is:

1. A computer-implemented method for training a software infrastructure,
    wherein the software infrastructure is based on machine-learning techniques and intended to analyse data obtained from a non-tomographic instrumental examination of objects of a pre-determined type in order to determine information on characteristics of interest of those objects, wherein, moreover, each of the objects has been obtained by splitting a product into pieces;
    wherein the data obtained from the instrumental examination are in electronic format;
    wherein, once a training set comprising a plurality of training objects of a predetermined type has been chosen, training input data and the corresponding training output data are fed into the software infrastructure for each training object;
    wherein the training input data for each training object comprise the data obtained from the instrumental examination on that training object;
    wherein the training output data for each training object comprise information on the characteristics of interest of the training object;
    wherein the information on the characteristics of interest is, at least in part, information that has been obtained from the results of a tomographic examination of the product from which the training object was obtained;
    and wherein the software infrastructure processes, through its own training unit, the training input data and the training output data for each training object in order to set internal processing parameters of the software infrastructure which correlate the training input data to the training output data.

2. A computer-implemented method according to claim 1, further comprising a sequence for preparing training output data, encompassing the following operating steps:
    a tomography step in which a tomographic examination is performed of a product using an electronic tomograph, from which said results of the tomographic examination are obtained;
    a splitting step in which the product is split into a plurality of different training objects using a mechanical device;
    a computerised correlation step in which each training object obtained as above is correlated to its position within the product the training object has been obtained from and/or to at least part of said results of the tomographic examination on the product the training object has been obtained from;
    a computerised processing step based on the results of the correlation step in which the results of the tomographic examination are processed to determine information on the characteristics of interest of each training object.

3. A computer-implemented method according to claim 2, further comprising a step for instrumental examination of each training object in order to obtain the relative training input data.

4. A computer-implemented method according to claim 1, wherein the data obtained from the instrumental examination are composed of a two-dimensional electronic map showing the object or a part thereof, with the electronic map comprising a plurality of cells with at least one value assigned to each.

5. A computer-implemented method according to claim 4, wherein the training input data consist of one or more groups of electronic data, wherein each group corresponds to a two-dimensional image.

6. A computer-implemented method according to claim 1, wherein the method is implemented by one or more management and control computers of a product processing facility, wherein the facility comprises:
    one cutting station in which each product is split into a plurality of objects; and one control station in which one or more instrumental examinations are performed on the objects which have been obtained by splitting the product and in which input data are obtained for the objects.

7. A computer-implemented method according to claim 6, wherein the software infrastructure is associated with the control station and wherein the software infrastructure also comprises a processing unit which uses the internal processing parameters set by the training unit to determine information on the characteristics of interest of objects by correlating the input data for each object to the output data.

8. A computer-implemented method according to claim 6, wherein the facility also comprises a tomography station, located upstream from the cutting station, wherein the three-dimensional tomographic examination of each product is performed, and wherein the training output data for each object are obtained from the one or more management and control computers by processing the results given by the tomography station.

9. A computer-implemented method according to claim 8, wherein the training input data and the training output data are generated for each object without interrupting the operation of the processing facility, and wherein these data are used by the training unit of the software infrastructure during the ordinary use of the facility in order to perform a further setting of the internal processing parameters of the software infrastructure.

10. A computer-implemented method according to claim 1, wherein:
there are an initialisation step in which a training set is created comprising a plurality of training objects, and a plurality of expansion steps in each of which one or more training objects are added to the training set;
the training unit processes the training input data and the training output data for each training object in order to set internal processing parameters for the software infrastructure which will correlate the training input data to the training output data both after the initialisation step and after each expansion step.

11. A computer-implemented method according to claim 10, wherein the objects added to the training set in each expansion step are objects to which the software infrastructure, through its own processing unit, has previously applied the machine-learning techniques to analyse the data obtained from the instrumental examination on those same objects for the purpose of determining information on the characteristics of interest of those objects.

12. A computer-implemented method according to claim 1, wherein the software infrastructure comprises a neural network, a deep neural network, a convolutional neural network or a combination of two or more of the above.

13. A computer-implemented method according to claim 1, wherein said objects are wooden boards, wherein said products are wooden logs.

14. A computer-implemented method according to claim 13, wherein the data obtained from the instrumental examination are in electronic format and correspond to images of the wooden board surface within the visible light range on one or more wavelength bands, to images of the wooden board surface outside the visible light range on one or more wavelength bands, to images of the wooden board surface illuminated to highlight the presence of scattering, to images obtained by performing x-rays of the wooden boards, to measurements of the object's vibration frequency spectrum or to a combination of one or more of the above.

15. A computer-implemented method according to claim 13, wherein the characteristics of interest are the presence or not on the board of wood features or defects and/or the position of these characteristics or defects relative to the board.

16. A computer-implemented method according to claim 1, wherein the characteristics of interest are expressed in terms of a plurality of classes.

17. A computer-implemented method according to claim 16, wherein the characteristics of interest are the position of wood features or defects relative to the board, and wherein each class corresponds to such position being within a space volume located inside or outside of the board.

18. A computer-implemented method for detecting characteristics of interest of an object of a predetermined type, wherein the computer-implemented method includes the use of a software infrastructure based on machine-learning techniques, wherein the software infrastructure uses as the input data electronic data obtained from an instrumental examination on said object, wherein the software infrastructure used is trained by a computer-implemented method according to claim 1, and wherein the software infrastructure provides the characteristics of interest of the object as the output data.

19. A facility for splitting products into objects, wherein the facility comprises:
one or more management and control computers;
one cutting station in which each product is split into a plurality of objects; and
one control station in which one or more instrumental examinations are performed on the objects obtained from splitting each product;
and wherein the one or more control computers implement a method according to claim 18.

20. A facility according to claim 19, wherein the facility also comprises a tomography station in which the tomographic examination of each product is performed.

21. A facility according to claim 19, wherein the one or more control computers perform continuous training of the software infrastructure during the normal use of the facility, using a computer-implemented method;
wherein the software infrastructure is based on machine-learning techniques and intended to analyse data obtained from a non-tomographic instrumental examination of objects of a pre-determined type in order to determine information on characteristics of interest of those objects, wherein, moreover, each of the objects has been obtained by splitting a product into pieces;
wherein the data obtained from the instrumental examination are in electronic format;
wherein, once a training set comprising a plurality of training objects of a predetermined type has been chosen, training input data and the corresponding training output data are fed into the software infrastructure for each training object;
wherein the training input data for each training object comprise the data obtained from the instrumental examination on that training object;
wherein the training output data for each training object comprise information on the characteristics of interest of the training object;
wherein the information on the characteristics of interest is, at least in part, information that has been obtained from the results of a tomographic examination of the product from which the training object was obtained;
and wherein the software infrastructure processes, through its own training unit, the training input data and the training output data for each training object in order to set internal processing parameters of the software infrastructure which correlate the training input data to the training output data.

* * * * *